US00PP07922P

United States Patent [19]

Marciel

[11] Patent Number: Plant 7,922

[45] Date of Patent: Jul. 28, 1992

[54] ROSE PLANT NAMED DEVORNIT

[75] Inventor: Stanley G. Marciel, Aptos, Calif.

[73] Assignee: DeVor Nurseriers, Inc., Watsonville, Calif.

[21] Appl. No.: 653,910

[22] Filed: Feb. 12, 1991

[51] Int. Cl.[5] ..... A01H 5/00

[52] U.S. Cl. ..... Plt./21

[58] Field of Search ..... Plt. 20, 21

*Primary Examiner*—James R. Feyrer

[57] ABSTRACT

A new and distinct greenhouse rose particularly distinguished by its continuous and profuse production of relatively small cardinal red colored flowers. These long lasting flowers are borne on sturdy upright stems of a vigorous upright plant of about 105 cm. in height, having small and abundant foliage.

1 Drawing Sheet

BACKGROUND OF THE INVENTION

This new rose plant originated as a seedling hybrid resulting from my crossing an unnamed but numbered seedling selected from the collection of rose plants maintained in my nursery at Pleasanton, Calif. for breeding purposes, with pollen of the variety Mary DeVor (U.S. Plant Pat. No. 2,838). Because of the pleasing coloration of the abundant small blooms of this plant, and its vigorous growth habit, I propagated this seedling by budding at Pleasanton. Subsequently I decided that this plant was an ideal subject for commercial propagation and tests for commercial suitability and propagation homogeneity was done under my direction by budding at my nursery in Wasco, Calif. This was done through several generations at Wasco which demonstrated satisfactorily that the novel characteristics of this new plant would hold true for generation to generation and appear to be firmly fixed.

DESCRIPTION OF THE DRAWING

A new rose plant is illustrated by the accompanying full color photographic drawing which shows a face view of a fully opened flower, the colors shown being as nearly true to those herein specified as is reasonably possible to obtain by conventional photographic procedures.

DESCRIPTION OF THE NEW VARIETY

The following is a detailed description of my new rose plant based upon observation of plants grown in greenhouse at Wasco, with the color designations specified herein being according to The R.H.S. Colour Chart published by The Royal Horticultural Society of London, England.

THE PLANT

Origin: Seedling.

Parentage:

*Seed parent.*—Unnamed but numbered seedling selected from a collection of breeding plants at Pleasanton, Calif.

*Pollen parent.*—Mary DeVor, U.S. Plant Pat. No. 2,838.

Classification:

*Botanic.*—Hybrid tea.

*Commercial.*—Greenhouse rose.

Form: An upright vigorous free branching bush.

Height: Approximately 155 cm. high.

Growth habit: Vigorous and sturdy.

Main stem:

*Length.*—About 43 cm.–47 cm. from the last flower cut.

*Color.*—Yellow-Green, 146-A.

*Branching character.*—Free branching.

Foliage:

*Quantity.*—Abundant.

*Number of leaves.*—About 7 to 8 from the last flower cut.

*Size.*—About 65 mm. long.

Leaflets:

*Number.*—Three to 7.

*Shape.*—Ovate with denticulate margin.

*Size.*—About 66 mm. by 26 mm. long.

*Texture.*—Semi-leathery.

*Aspect.*—Smooth and semi-glossy.

*Color.*—Upper side — Yellow green 147-A. Under side — Yellow green 147-B with Grey-Purple 183-C spots.

Stipules: Hairy adnate.

Rachis length: About 65 mm. on leaf having 7 leaflets; about 22 mm. on leaf having 3 leaflets.

Petioles: About 5½ mm. long on leaf having 7 leaflets and about 11 mm. long on leaf having three leaflets.

Ribs and veins: Slightly grooved on top and slightly rounded on bottom.

Thorns:

*Size.*—Varying in size, approximately 10 mm. long.

*Color.*—Yellow-Green 146-D.

THE BUD

Size: Small.

*Diameter.*—About 19 mm.

*Length.*—About 34 mm.

Shape: High-centered and pointed with sightly tapering sides.

Rate of opening: Slow.

Color of petals:

*When sepals first divide.*—53-A.

*When petals begin to unfurl.*—Red 53-A.

Sepals:

*Number.*—Five.

*Shape.*—Spreading with small leafs protruding from some.

*Character.*—The sepals curl back when flowers open.

*Color.*—Inside — Yellow-Green 144-A. Outside — Yellow-Green 144-B; some with small white hairs covering calyx.

Calyx:

*Shape.*—Funnel shaped.

*Width.*—About 8½ mm.

*Length.*—About 5 mm.

*Size.*—Small.

*Splitting.*—Calyx does not split.

*Aspect.*—Smooth.

Flower stem:

*Length.*—About 82 to 91 mm.

*Character.*—Slender and erect.

*Color.*—Yellow-Green 144-A.

THE FLOWER

Blooming habit: Continuous and abundant from early Spring through mid-season and Fall, blooming freely under greenhouse conditions.

Size of bloom: Small.

*Diameter.*—84½ mm.

*Depth.*—About 28 mm.

Borne: Singly on sturdy, upright stems.

Shape:

*When bloom first opens.*—High center.

*When bloom matures.*—Tight cup, the petals becoming nicely imbricated.

Petalage:

*Number.*—Approximately 34 to 38.

*Arrangement.*—Imbricated.

*Form.*—Spear shaped with lobed margins that curl under to create a point.

*Texture.*—Semi-leathery, but soft.

*Appearance.*—Velvety.

*Color.*—Outer petals — Cardinal Red 53-A with base of Yellow 4-C. Reverse side — Red-Purple 60-B with a base of Yellow-D and Red-Purple 59-D, just above base. Inside petals — Cardinal Red 53-A with a base of Yellow 3-D. Reverse side — Red-Purple 60-A with a base of Yellow 2-C.

Petaloids:

*Number.*—Seven.

*Size.*—About 18 mm.

*Color.*—Red 53-A with a base of Yellow 14-A with a stripe of 155-D upwards.

Flower stem:

*Length.*—About 82 to 91 mm.

*Color.*—Yellow-Green 144-A.

*Character.*—Sturdy and upright.

Fragrance: Strong, musk fragrance.

Persistence: In greenhouse environment, flower hangs on and dries.

Discoloration after full bloom: Very slight, if at all.

Disease resistance: Resistant to mildew, rust, and black spots as observed at Watsonville, Calif.

Lasting quality: On the plant, and as a cut flower, very long lasting.

THE REPRODUCTIVE ORGANS

Stamens:

*Number.*—Seventy-one.

*Arrangement.*—Introrse.

*Anthers.*—Size: About 2 mm. Color: Yellow-Orange 21-C.

*Filaments.*—Length: About 4 to 5 mm. Color; Red 54-B fading to Yellow 10-D.

*Pollen.*—Color: Yellow-Orange 21-C.

Pistils:

*Number.*—Approximately 83.

*Styles.*—Length: About 9 to 10½ mm. Color: Red 51-A.

*Stigmas.*—Color: Red group 49-D fading to Red 54-B and then to Red 36-D.

Character of the ovaries: Round, but elongated and covered with silver.

Fruit:

*Fertility.*—The fruit is fertile.

I claim:

1. A new and distinct variety of rose plant, substantially as herein shown and described, characterized by its profuse and continuous production of small cardinal red flowers, which have a long lasting vase life; by its vigorous and free branching growth habit and its sturdy upright stems.

* * * * *

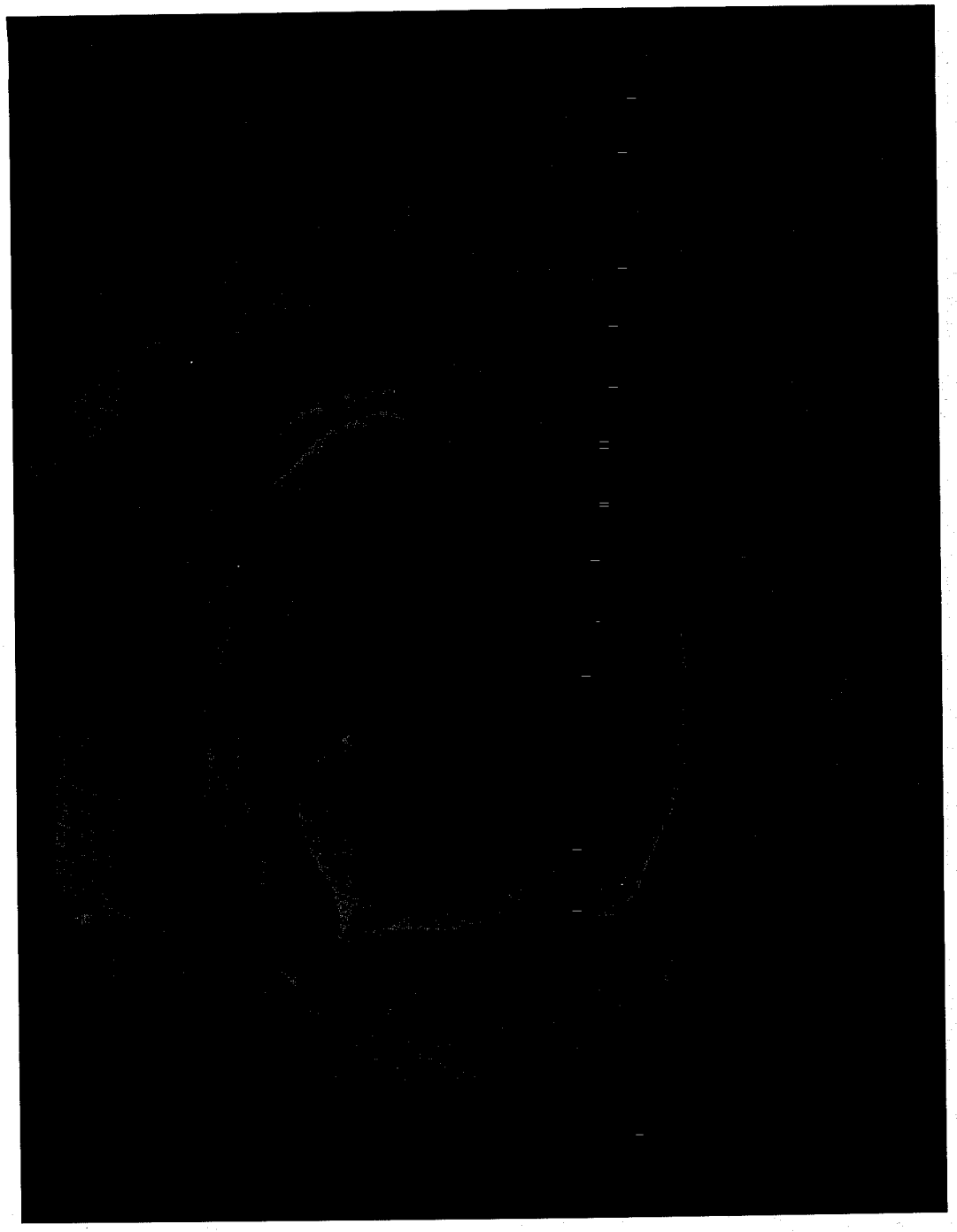

UNITED STATES PATENT AND TRADEMARK OFFICE

CERTIFICATE OF CORRECTION

PATENT NO. : Plant 7,922

DATED : July 28, 1992

INVENTOR(S) : Stanley G. Marciel

It is certified that error appears in the above-identified patent and that said Letters Patent is hereby corrected as shown below:

Column 1, Line 1 - delete "Invention" and insert --New Plant--.

Signed and Sealed this

Thirty-first Day of August, 1993

Bruce Lehman

*Attest:*

BRUCE LEHMAN

*Attesting Officer*

*Commissioner of Patents and Trademarks*